United States Patent [19]

Moore

[11] Patent Number: 4,469,335
[45] Date of Patent: Sep. 4, 1984

[54] SEALING APPARATUS WITH SEALING DEVICE OPERABLE UNDER PRESSURE DIFFERENTIAL ESTABLISHED THEREACROSS

[75] Inventor: Vincent Moore, Mercer Island, Wash.

[73] Assignee: American Sterilizer Company, Erie, Pa.

[21] Appl. No.: 400,727

[22] Filed: Jul. 22, 1982

[51] Int. Cl.³ .............................................. F16J 15/46
[52] U.S. Cl. .................................... 277/27; 277/59; 277/75; 277/152; 49/477
[58] Field of Search ................. 277/1, 3, DIG. 7, 27, 277/226, 70, 71, 72 R, 9, 15, 72 FM, 75, 76, 66, 130–132, 74, 187, 152, 153, 34, 34.3, 34.6, 59; 49/475, 477, 485

[56] References Cited

U.S. PATENT DOCUMENTS

| 1,037,647 | 9/1912 | London | 277/27 X |
| 2,864,258 | 12/1958 | Klingler | 277/75 X |
| 3,144,035 | 8/1964 | Hablanian et al. | 277/1 X |
| 3,831,950 | 8/1974 | Bentley et al. | 49/475 X |
| 3,858,372 | 1/1975 | Wilson | 52/81 |
| 4,103,912 | 8/1978 | Thomé | 277/DIG. 7 |
| 4,337,956 | 7/1982 | Hopper | 277/59 X |

FOREIGN PATENT DOCUMENTS

| 1505744 | 8/1970 | Fed. Rep. of Germany | 49/477 |
| 880243 | 12/1942 | France | 277/153 |
| 606032 | 8/1948 | United Kingdom | 277/27 |
| 950062 | 2/1964 | United Kingdom | 49/477 |
| 2076907 | 12/1981 | United Kingdom | 277/173 |

Primary Examiner—Robert S. Ward
Attorney, Agent, or Firm—Robert D. Yeager; Andrew J. Cornelius

[57] ABSTRACT

Sealing apparatus seals the opening of a chamber by seating a double lip seal—or a functionally equivalent seal—between the chamber and the door of the chamber when there is an insufficient pressure differential across the seal to seat it properly. The apparatus includes a vacuum pump which evacuates air from the enclosed space defined by the chamber, the chamber door, and the two flexible members of the sealing device to force the sealing device against the chamber and the chamber door. A storage tank can be provided which can be evacuated of fluid to reduce the capacity of the vacuum pump, or to eliminate it altogether when the sealing apparatus is used with a chamber equipped with a vacuum pump.

2 Claims, 3 Drawing Figures

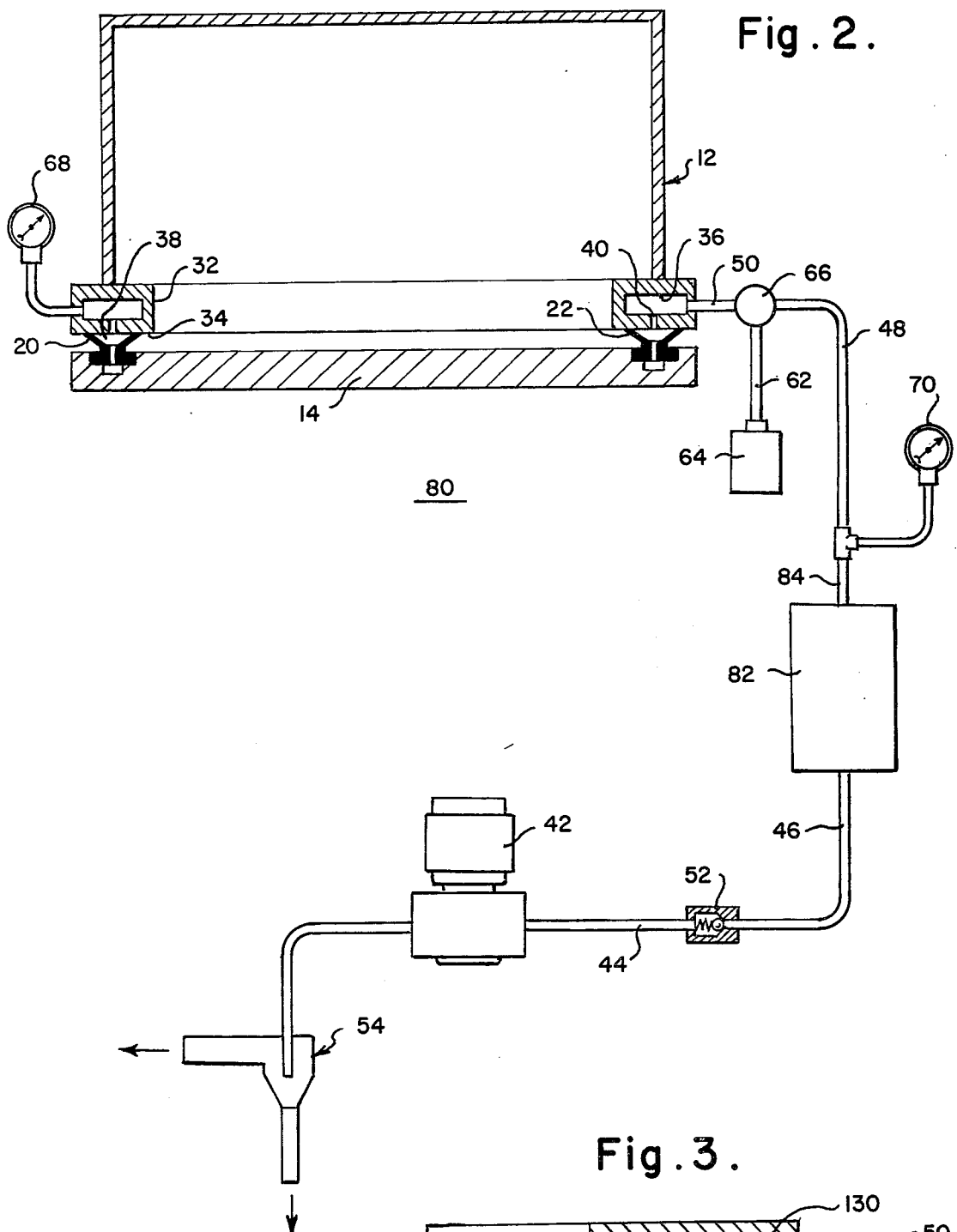

SEALING APPARATUS WITH SEALING DEVICE OPERABLE UNDER PRESSURE DIFFERENTIAL ESTABLISHED THEREACROSS

BACKGROUND OF THE INVENTION

1. Field of the Invention

The present invention relates generally to apparatus for inhibiting the flow of fluid between two confronting surfaces and, more particularly, to such apparatus that includes a flexible sealing device.

2. Description of the Prior Art

Lip seals are commonly used to inhibit the flow of fluid to or from the interior of such pressure chambers as sterilizer chambers. Lip seals operate to seal a chamber opening when a pressure differential of a minimum predetermined amount is present across the seal. The existence of the pressure differential causes the seal to be forced against one of the surfaces between which it is disposed when the chamber is closed to seal the opening.

Generally, a lip seal includes a base member which extends along and is mounted to either the end ring or the door of the sterilizer. One type of lip seal—a double lip seal—includes a pair of flexible members extending from the base member along its entire length. The base member and the flexible members are adapted to make contact with the end ring of the sterilizer chamber and the door when the door is in its closed position in which it confronts the end ring. It is common for the base member to be mounted to the door and the free ends of the flexible members to be in contact with the end ring when the door is in its closed position. In such a configuration, the flexible members and the end ring define an enclosed space.

To ensure proper operation of the sterilizer closure—that is to ensure that the flow of fluid to and from the sterilizer chamber is inhibited sufficiently—a force must be exerted on either the interior lip—the lip that is exposed to the fluid within the chamber—if the chamber is under positive pressure, or the exterior lip—the lip that is exposed to the atmosphere—if the chamber is under a vacuum, of a magnitude sufficient to force the lip against the end ring and prevent fluid flow between the lip and the end ring.

Sterilizers which use a compression seal to seal the opening of the sterilizer chamber must include expensive and mechanically complicated equipment for compressing the seal between the sterilizer door and the end ring. Sterilizers which use a lip seal need not include such equipment since the lip seal need not be compressed between the door and the end ring to operate properly.

However, it has not been possible to use lip seals to effectively seal some types of chambers. For example, a washer sterilizer must contain a substantial amount of water in an otherwise unpressurized chamber. Lip seals have been unsuitable for use with washer sterilizers because the water in the vicinity of the water line within the chamber cannot establish a pressure differential across the seal of a magnitude that is sufficient to cause proper seating of the seal against the end ring; thus, some water escapes from the chamber. Accordingly, compression seals are commonly used to seal the opening of washer sterilizers.

Further, although double lip seals can be used advantageously with chambers which operate under positive gaseous pressure or a vacuum, some leakage of gas from the chamber may occur when the chamber is brought from a state of substantially zero pressure to a positive gaseous pressure by the introduction of gas to the chamber. Since some gases used in sterilizer chambers can pose a health hazard to hospital personnel who are exposed to them, it is desirable to avoid such gas leakage.

SUMMARY OF THE INVENTION

The present invention renders effective the use of a double lip seal and functionally equivalent seals to inhibit fluid flow between two surfaces in applications where the pressure differential across the seal would be insufficient otherwise to seat the seal and permit it to function properly. For example, the present invention permits use of a double lip seal to seal the opening of a washer sterilizer where the pressure exerted by the water in the sterilizer chamber near the water line is insufficient to properly seat the seal.

The present invention provides apparatus for inhibiting the flow of fluid between two confronting surfaces by creating a pressure differential across a sealing device disposed between and in contact with the surfaces. The sealing device includes a flexible portion which cooperates with one surface to define an enclosed space. The flexible portion can include a base adapted to engage one surface and a pair of flexible members extending from the base that are adapted to contact the other surface. The present invention also includes apparatus in fluid communication with the enclosed space for creating the pressure differential by reducing the pressure exerted by fluid disposed within the enclosed space on the flexible portion and the surface with which the flexible portion is in contact.

The present invention also provides improved apparatus for sealing the opening of a chamber which has apparatus for evacuating the chamber. The sealing apparatus is of the type including a door which can be placed in a closed position in which it confronts the chamber opening and a sealing device which is in contact with the chamber and the door when the door is in its closed position. The sealing device seals the chamber opening when the door is in its closed position and a pressure differential is established across the sealing device.

The sealing device has a flexible portion which is adapted to assume an engaged position in which it is in contact with the chamber and the door and in which it is seated to cooperate with the chamber and the door to define an enclosed space. The flexible portion is so adapted as to be unseated by fluid flowing from a second chamber into the chamber when the pressure within the second chamber is greater, by a predetermined amount, than the pressure within the chamber to permit the evacuating apparatus of the chamber to evacuate the second chamber to an extent sufficient to substantially equalize the pressure in the two chambers. The evacuated second chamber operates the sealing device when it is placed in fluid communication with the enclosed space defined by the flexible portion of the seal and when the pressure within the second chamber is lower than the pressure within the chamber by a predetermined amount.

BRIEF DESCRIPTION OF THE DRAWINGS

The following detailed description of the preferred embodiment can be understood better if reference is made to the drawings, in which:

FIG. 2 is a graphic view of a sterilizer chamber and an alternate embodiment of the present invention; and FIG. 3 is a detail view showing an alternate mounting for the lip seal.

DETAILED DESCRIPTION OF THE PREFERRED EMBODIMENTS

Figure 1:
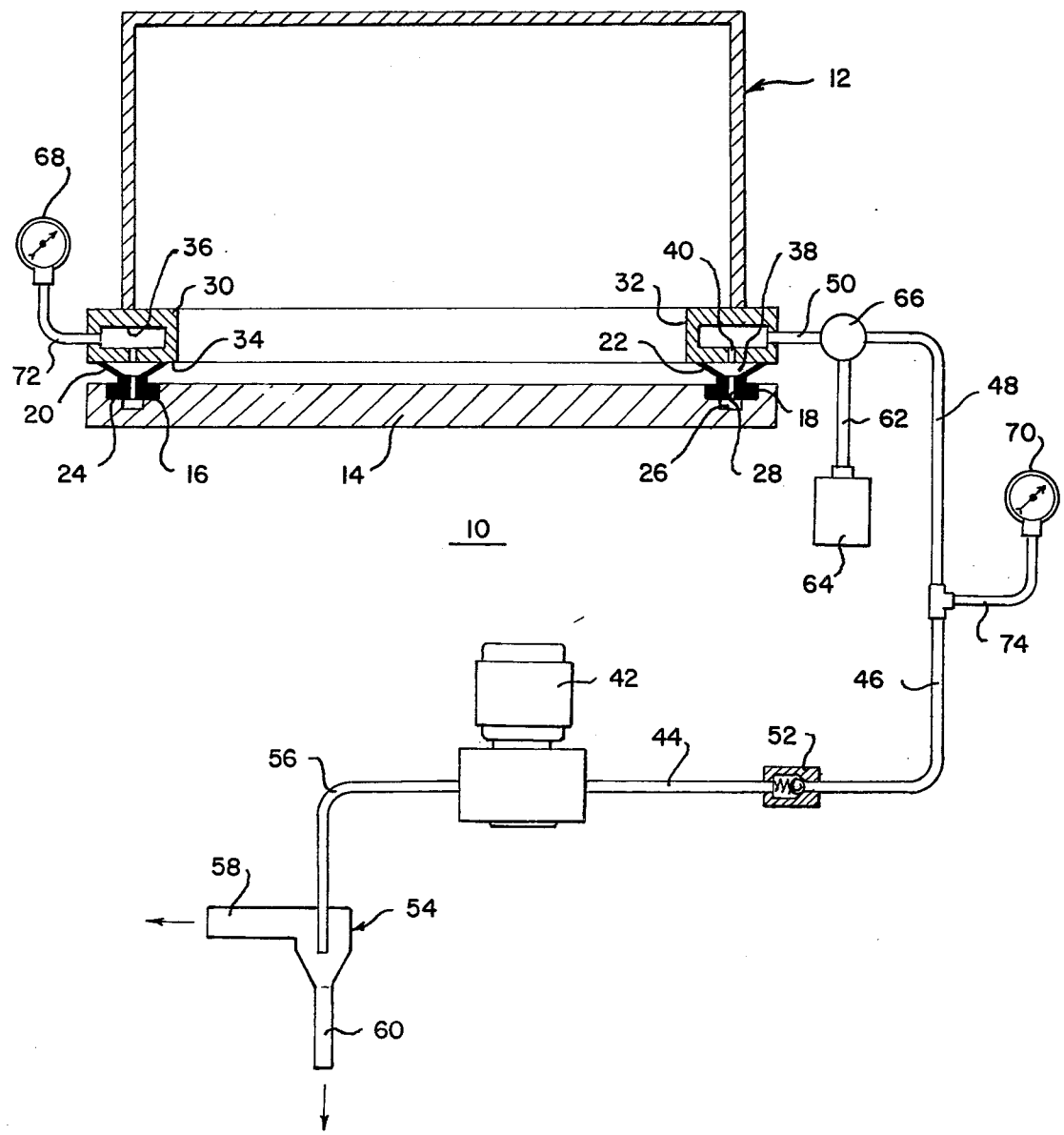
FIG. 1 is a graphic view of a sterilizer chamber and a preferred embodiment of the present invention.

FIG. 1 shows sealing apparatus 10 mounted to a sterilizer chamber 12. Sealing apparatus 10 includes a chamber door 14 to which a double lip seal 16 is mounted. Seal 16 includes a base member 18 and lip members 20 and 22. Base member 16 is received by a groove 24 formed in the entire perimeter of door 14. Sterilizer 12 includes an end ring 30 which defines the sterilizer chamber opening 32. The free ends of flexible lips 20 and 22 bear against surface 34 of end ring 32 when door 14 is in its closed position—the position shown in FIG. 1. Seal 16 seals opening 32 when a pressure differential exists across seal 16. Accordingly, opening 32 is sealed when sterilizer chamber 12 is under positive pressure, and interior lip 22 is forced against surface 34 or when sterilizer chamber 12 is under a vacuum and flexible lip 20 is forced against surface 34.

End ring 30 defines a longitudinal passage 36. When door 14 is in its closed position, flexible lips 20 and 22 and surface 34 of end ring 30 define an enclosed passage or space 38. A plurality of passages 40 are formed in end ring 30 and provide fluid communication between passage 36 and enclosed space 38.

A vacuum pump 42 is placed in fluid communication with passage 36 and enlosed space 38 through connectors 44, 46, 48, and 50. A check valve 52 is connected to lines 44 and 46 and prevents fluid flow from pump 42 to chamber 12. A gas scavenger and drain 54 disposes of any gas or liquid drawn from sterilizer chamber 12 by vacuum pump 42. Gas scavenger and drain 54 communicates with vacuum pump 42 through line 56. Any gas flowing in line 56 is drawn through outlet 58 by the gas scavenging system and any liquid flowing through line 56 passes to the sewage system through drain 60.

The sealing apparatus 10 creates a vacuum in enclosed space 38 which forces lips 20 and 22 of sealing device 16 against surface 34. Air from enclosed space 38 is pulled by vacuum pump 42 through passages 40, passage 36, lines 50, 48, and 46, check valve 52, lines 44 and 56, and gas scavenger and drain 54.

A vent line 62 is connected to lines 48 and 50 with a suitable conventional control valve 66. A microbial filter 64 can be connected to vent line 62 and control valve 66, if desired. Control valve 66 is of a type that can be manipulated to vent enclosed space 38 to the atmosphere through vent line 62 prior to moving door 14 from its closed position. Microbial filter 64 removes harmful organisms from air admitted to passage 36 and space 38 before they are vented. Further, control valve 66 can be placed in positions in which lines 48 and 50 are in fluid communication with each other or are isolated from each other.

Pressure gauges 68 and 70 can be provided to measure the pressure drop developed within enclosed space 38. Pressure gauge 68 communicates with passage 36 through line 72. Line 72 enters passage 36 at a location remote from that at which line 50 communicates with passage 36. Accordingly, pressure gauge 68 provides an indication of the actual pressure within enclosed space 38. Pressure gauge 70 communicates with lines 48 and 46 through line 74. Gauge 70 communicates with lines 46 and 48 at a location relatively close to the inlet of vacuum pump 42 and, accordingly, provides an indication of the vacuum level theoretically provided by vacuum pump 42. By comparing the readings of gauges 68 and 70, the pressure drop within enclosed space 38 and, accordingly, an indication of the extent of fluid leakage from passage 36 due to seal wear or malfunction can be obtained.

It is preferable that sealing apparatus 10 include a second groove 26 and passages 28 which provide fluid communication between enclosed space 38 and groove 26. Any fluid that escapes from chamber 12 between base member 18 of seal 16 and groove 26 will be pulled by pump 42 through passages 28 and, accordingly, prevented from escaping sealing apparatus 10.

Although base 18 of sealing device 16 of the preferred embodiment is mounted to door 14, base 18 can be mounted to the end ring of the sterilizer chamber, as shown in FIG. 3. If base member 18 is mounted to end ring 130, the inlet of line 50 still should be secured to end ring 130 to avoid the need for complicated apparatus that would be necessary to enable connection of line 50 to movable door 14. As shown in FIG. 3, passages 122 formed in seal 116 provide fluid communication between enclosed space 138 and line 50 through groove 126.

FIG. 2 shows an alternate embodiment of the present invention. Sealing apparatus 80 is identical to sealing device 10 except for the presence in sealing apparatus 80 of a storage tank 82. Storage tank 82 communicates with vacuum pump 42 through lines 46 and 44 and check valve 52 and with passage 36 through lines 50, 48, and 84 and control valve 66. Storage tank 82 can be evacuated by pump 42 and used to provide an initial vacuum surge to evacuate enclosed space 38. Accordingly, sealing apparatus 80 need not include a vacuum pump 42 of as great a capacity as needed by such apparatus not having a tank 82. Also, control valve 66 of sealing apparatus 80 must be of the type that permits three modes of operation. Control valve 66 must permit selective fluid communication between passage 36 and line 62, between line 48 and line 62, and between line 50 and line 48.

Further, a sterilizer chamber 12 that operates under positive pressure or a vacuum, and that includes a vacuum pump and sealing apparatus 80 need not include a vacuum pump 42. When the sterilizer chamber pump draws a vacuum in chamber 12, a vacuum can be drawn within tank 82—through the chamber 12, enclosed space 38, passages 40, and passage 36—when flexible lip 22 becomes unseated due to fluid flow from enclosed space 38 into sterilizer chamber 12. When the vacuum within chamber 12 is removed, lip 22 will again become seated and seal the vacuum within tank 82, thus preparing chamber 12 for the next sterilization cycle requiring sealing of opening 32. When the vacuum within the tank is no longer needed, the control valve 66 can be manipulated to bring line 48 into communication with vent line 62 to eliminate the vacuum within tank 82. It is necessary to include an initial vacuum cycle prior to initiating the normal sterilizer cycle to establish a vacuum within tank 82.

What is claimed is:

1. In apparatus for sealing the opening of a chamber, which has apparatus for evacuating the chamber, against the flow of fluid to and from the chamber, said apparatus being of the type including a door which can be placed in a closed position in which it confronts the chamber opening and a sealing device which is in contact with the chamber and said door to seal the chamber opening when said door is in its closed position and a pressure differential is established across said sealing device, said sealing device having a flexible portion which is adapted to assume an engaged position in which it is in contact with the chamber and said door and in which it is seated to cooperate with the chamber and said door to define an enclosed space, the improvement comprising:

a second chamber which can be placed in fluid communication with said enclosed space;

said flexible portion being so adapted as to be unseated by fluid flowing from said second chamber into the chamber when the pressure within said second chamber is greater by a predetermined amount than the pressure within the chamber to permit the evacuating apparatus of the chamber to evacuate said second chamber to an extent sufficient to substantially equalize the pressure in said chambers; and means for placing said second chamber in fluid communication with said enclosed space to permit said second chamber to evacuate said enclosed space when said second chamber is evacuated to a predetermined extent.

2. The apparatus recited in claim 1 wherein said sealing device includes a base and said flexible portion comprises a pair of flexible members extending from said base, said base and said flexible members being adapted to contact said chamber and said door.

* * * * *